United States Patent

Zollinger et al.

(12) United States Patent
(10) Patent No.: US 6,527,438 B2
(45) Date of Patent: Mar. 4, 2003

(54) AGGREGATE DILATOMETER DEVICE AND METHODS OF TESTING

(75) Inventors: Dan G. Zollinger, Bryan, TX (US); Tianxi Tang, Houston, TX (US)

(73) Assignee: The Texas A&M University System, College Station, TX (US)

(*) Notice: Subject to any disclaimer, the term of this patent is extended or adjusted under 35 U.S.C. 154(b) by 0 days.

(21) Appl. No.: 09/884,264

(22) Filed: Jun. 19, 2001

(65) Prior Publication Data
US 2002/0031165 A1 Mar. 14, 2002

Related U.S. Application Data
(60) Provisional application No. 60/213,054, filed on Jun. 21, 2000.

(51) Int. Cl.$^7$ .............................. G01N 25/16
(52) U.S. Cl. .......................... 374/56; 374/55
(58) Field of Search ...................... 374/55, 56

(56) References Cited

U.S. PATENT DOCUMENTS

| | | | |
|---|---|---|---|
| 2,831,340 A | * 4/1958 | Crandall et al. | 374/56 |
| 3,538,745 A | * 11/1970 | Wright et al. | 73/305 |
| 3,574,281 A | 4/1971 | Casey et al. | |
| 3,882,714 A | 5/1975 | Libal et al. | |
| 3,898,836 A | 8/1975 | Clusener | |
| 4,506,547 A | * 3/1985 | Kunze et al. | 73/150 R |
| 4,852,054 A | * 7/1989 | Mastandrea | 364/509 |
| 4,923,307 A | 5/1990 | Gilmore et al. | |
| 4,976,549 A | * 12/1990 | Khan | 324/713 |
| 5,121,987 A | 6/1992 | Berg | |
| 5,172,977 A | 12/1992 | Enustun et al. | |

FOREIGN PATENT DOCUMENTS

JP  01174449  3/1989
JP  03262948  11/1991

OTHER PUBLICATIONS

Database WPI Section EI, Week 197551, Derwent Publications, Ltd., London, GB, AN 1975–N5227W XP002206707 and SU 452777A (Tula Poly) Dec. 25, 1974.

* cited by examiner

Primary Examiner—Diego Gutierrez
Assistant Examiner—Lydia M. De Jesús
(74) Attorney, Agent, or Firm—Bracewell & Patterson, L.L.P.

(57) ABSTRACT

Methods and devices for improved measurement of the thermal expansion and/or chemical reactivity of aggregates used in concrete and for similar substances. Aggregate is placed into the chamber of a metallic container having an enlarged opening. The aggregate is placed in a water bath, and a tightly sealable lid is placed onto the container. The lid carries a linear variable differential transducer (LVDT). A thermocouple for sensing temperature is also retained within the lid so that a sensor on the thermocouple contacts the water bath when the lid is secured onto the container. The LVDT is operationally interconnected with a storage or recording device. In a preferred construction the lid retains a tower member having a float that is freely moveably mounted upon a guide rod. Movement of the float is indicative of a volumetric change in the aggregate and water. In operation, the dilatometer device is used to determine the information relating to the amount of expansion or contraction of the aggregate in response to thermal changes. In addition, the devices and methods of the present invention are useful for determining the degree of reactivity of the aggregate. The degree of volumetric change for the aggregate alone maybe determined using equations that isolate and remove the expansion quotient of the water.

15 Claims, 3 Drawing Sheets

AGGREGATE DILATOMETER DEVICE AND METHODS OF TESTING

CROSS-REFERENCE TO RELATED APPLICATIONS

This application claims the benefit of U.S. Provisional Patent Application No. 60/213,054 filed Jun. 21, 2000.

BACKGROUND OF THE INVENTION

1. Field of the Invention

The invention relates generally to devices and methods that are useful for measuring the thermal expansion and/or chemical reactivity of aggregates used in concrete and like substances.

2. Description of the Related Art

Techniques for determining the coefficient of thermal expansion, and related expansion information, for a particular aggregate type are important, as such properties determine the thermal expansion of concrete using that aggregate type to a considerable degree. Techniques for determining the chemical reactivity of aggregate types are important for similar reasons. Chemically reactive aggregates can expand greatly over time inside a concrete mixture, which may lead to cracking thereby weakening the structure of the concrete.

To date, techniques for determining information concerning the expansion of aggregates and substances containing aggregates have generally involved the use of flasks to contain crushed pieces of aggregate mixed with water. To measure aggregate expansion, these arrangements also relied upon a readings of the levels of a delicate balance of water and mercury contained in a complex arrangements of tubes and stopcocks. These prior art techniques were also relatively limited, of questionable accuracy and incapable of measurements over wide temperatures.

Further, such techniques (which were limited to thermal expansion testing) provided no reliable means of determining the actual temperature of the aggregate being tested. Instead, it was assumed that the aggregate samples were at the same temperature as the water bath surrounding the flask.

Other methods of determining information relating to the expansion of aggregate utilized direct measurement of individual aggregates by placing chunk aggregate members inside a clamp or similar retainer and gauging how much the individual member expands as temperature is changed. Unfortunately, information obtained from this type of measurement is not accurately generalized to larger amounts of aggregates.

Existing alkali silica reaction (ASR) techniques for testing the chemical reactivity of aggregates also have significant limitations. These tests do not always provide reliable results or results that maybe applicable to the prediction of performance under similar conditions in the field.

The invention addresses the problems of the prior art.

SUMMARY OF THE INVENTION

The invention provides methods and devices for improved measurement of the thermal expansion and/or chemical reactivity of aggregates used in concrete and for similar substances. In a preferred embodiment, aggregate is placed into the chamber of a metallic container having an enlarged opening. The aggregate is placed in a water bath, and a tightly sealable lid is placed onto the container. The lid carries a linear variable differential transducer (LVDT). A thermocouple for sensing temperature is also retained within the lid so that a sensor on the thermocouple contacts the water bath when the lid is secured onto the container. The LVDT is operationally interconnected with a storage or recording device. In a preferred construction the lid retains a tower member having a float that is freely moveably mounted upon a guide rod. Movement of the float is indicative of a volumetric change in the aggregate and water.

In operation, the dilatometer device is used to determine the information relating to the amount of expansion or contraction of the aggregate in response to thermal changes. In addition, the devices and methods of the present invention are useful for determining the degree of reactivity of the aggregate. Preferably, he dilatometer is calibrated before use with aggregate by filling the container with water alone and then determining the thermal expansion associated with the water in the particular container being used. The degree of volumetric change for the aggregate alone may be determined using equations that isolate and remove the expansion quotient of the water.

DETAILED DESCRIPTION OF THE PREFERRED EMBODIMENTS

Figure 1:
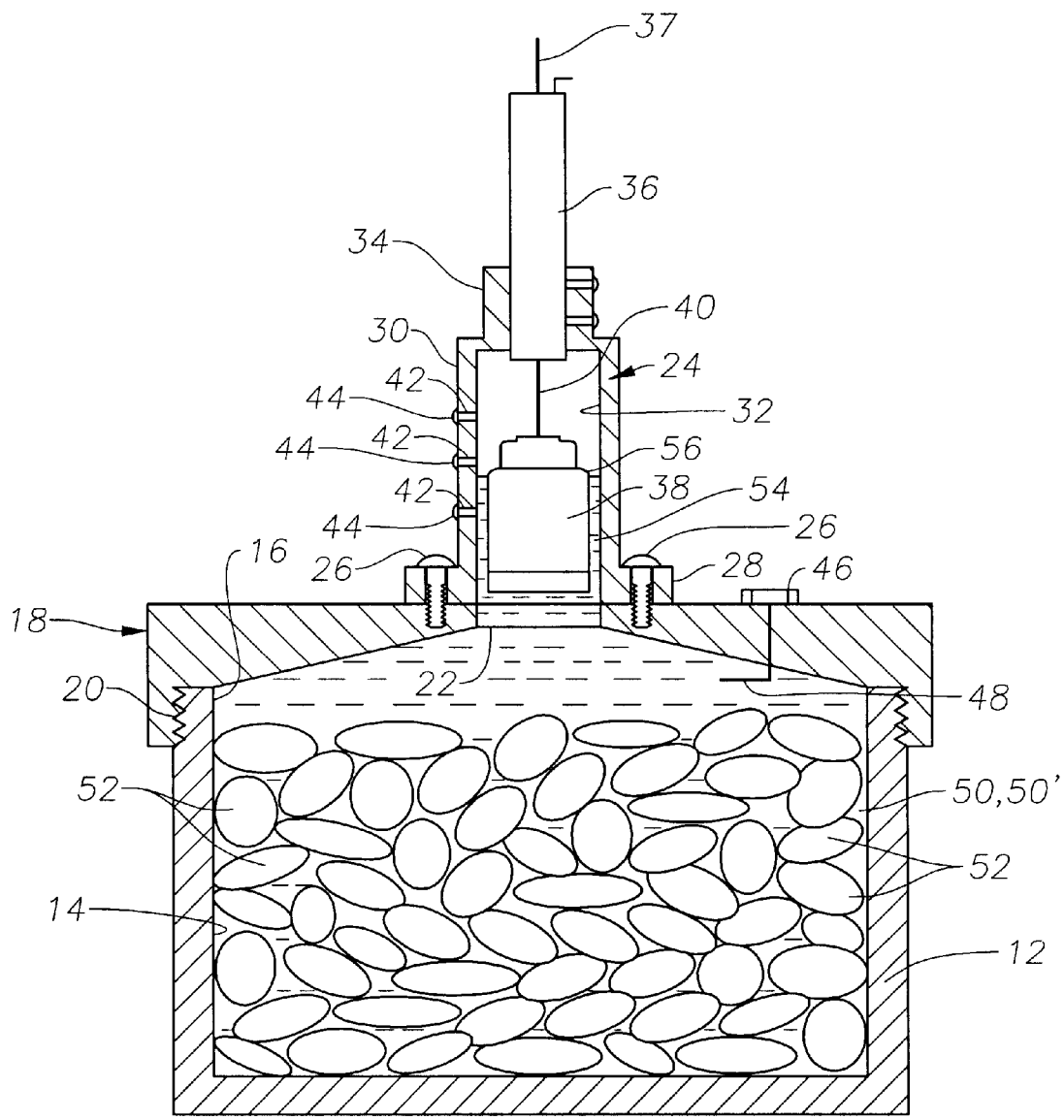
FIG. 1 is a side-cutaway view of an exemplary aggregate dilatometer device constructed in accordance with the present invention.

Referring to FIG. 1, there is shown an exemplary dilatometer device 10 that includes a cylindrical container 12 that is formed of a strong and durable material. It is presently preferred that the container 12 be fashioned of stainless steel or brass. The container 12 defines an interior chamber 14 with a large opening 16 at its upper end. It is preferred that the container 12 and its opening 16 have a diameter of approximately six (6) inches so that larger samples of aggregate or hardened concrete may be accommodated within its chamber 14 and permitted to expand and contract therein. A lid 18 is removably affixed to the container 12 by means of a threaded connection 20. The lid 18 contains a central aperture 22 and is preferably formed of stainless steel or brass.

A generally cylindrical tower member 24 is secured to the lid 18 by means of fasteners 26 which pass through a radially projecting flange 28 at the lower end of the tower section 24. The tower member 24 has a central section 30 that defines a cylindrical passage 32 therewithin. A reduced diameter portion 34 is located at the upper end of the tower member 24. Secured within the reduced diameter portion 34 is an apparatus 36 for determining an amount of expansion for a material within the chamber 14 of the container 12. A currently preferred apparatus 36 is a linear variable differential transducer (LVDT) of a type known in the art for sensing mechanical movement and generating an electrical signal indicative of such movement. The currently preferred LVDT is a UCAS/sCHAEVITZ Model MHR 0.050, which provides a voltage of 10.00 volts for a displacement of 1.27 mm. The apparatus 36 is electrically interconnected via lead 37 with a data storage or recording device of a type known in the art, such as a suitably programmed computer data acquisition device. Placement of the apparatus 36 within the tower member 24 is advantageous since the apparatus may be kept primarily above the level of the materials contained therein and, at the same time, be kept in contact with those materials for sensing of expansion.

The passage 32 of the tower member 24 retains a float 38 that is mounted upon guide rod 40 so that the float 38 is able to be moved freely upwardly and downwardly along the guide rod 40. In currently preferred embodiments, the float 38 is preferably made of glass, but maybe constructed of another material suitable for thermal or chemical expansion testing. It is further noted that the central section 30 of the tower member 24 has one or more fluid communication apertures 42 disposed therethrough. Plugs or screws 44 are removably disposed within the apertures 42 to close off fluid flow through the apertures 42.

A thermocouple 46 is disposed within the lid 18. The thermocouple 46 has a sensing element 48 that extends into the chamber 14 of the container 12 when the lid 18 is secured thereupon. Although not shown, it will be understood that the thermocouple 46 may be electronically interconnected to a monitor device (not shown), such as a computer having suitable monitoring software, such as Labtech Notebook. The thermocouple 46 is used to determine when the contents of the container 12 have been brought to specific, predetermined temperatures.

Prior to the testing of samples of aggregate, the device 10 must be calibrated. Calibration involves filling the container 12 with water 50 but no aggregate. The container 12 is then brought to the same first and second temperatures as will be used for the mixture of water 50 and aggregate 52. Readings indicative of the position of the float 38 are obtained by the LVDT 36 at both temperatures. An expansion curve may be developed that is representative of expansion for the dilatometer device 10 with water 50 alone.

FIG. 1 shows the chamber 14 of the container 12 being filled with water 50 and pieces of aggregate 52. It should be understood that, if it is desired to test concrete rather than aggregate, pieces (or a piece) of concrete will be substituted for the aggregate 52. A column of water 54 extends upwardly within the passage 32 of the tower member 24, ending at a water level 56. The column of water 54 floats the float 38, and the location of water level 56 is set by overfilling the column of water 54 and then removing a plug or screw 44 from one aperture 42 and allowing water to drain down until the water level 56 become even with the lower end of the aperture 42. If this is done with every test, a substantially constant water level 56 will be provided for each.

In operation for testing of aggregate samples, the container 12 of the dilatometer is filled with a mixture of water 50 and aggregate 52 and then the lid 18 is affixed to the container 12 allowing the sensing element to be disposed within the water 50. Prior to filling the container 12, it is desired to presoak the aggregate pieces 50 in water for at least 24 hours.

Figure 2:
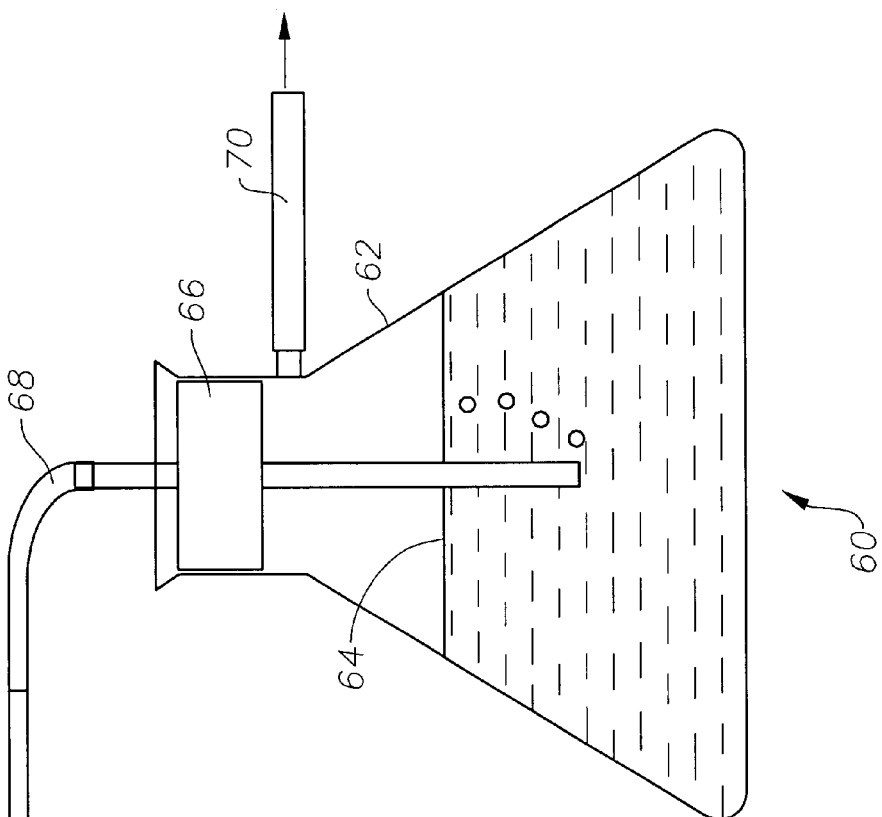
FIG. 2 is a side view of an arrangement for de-airing the dilatometer device illustrated in FIG. 1.
Figure 2:
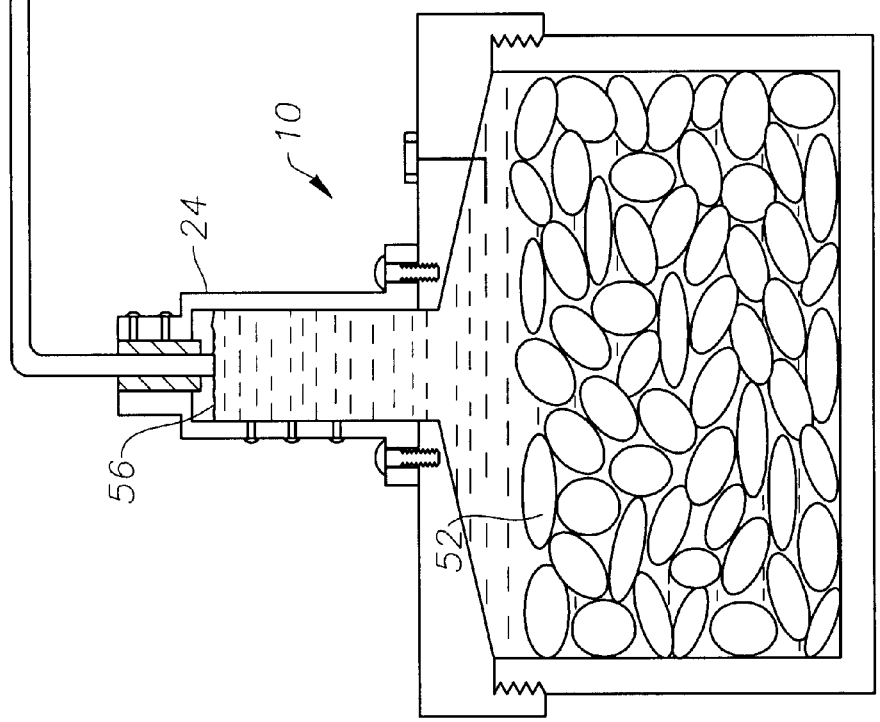

A de-airing operation is then performed (See FIG. 2) to help remove air from pores in the surface of the aggregate 52 and, thus, allow the aggregate 52 to be saturated more completely. A de-airing device 60 is interconnected to the dilatometer device 10. The exemplary de-airing device 60 is a flask 62 that is partially filled with water 64. The neck of the flask 62 contains a stopper 66. A first tube 68 is disposed through the stopper 66 and into the water 64. The first tube 68 extends into the tower member 24 of the dilatometer device 10 within which it is secured in an airtight manner. A second tube 70 extends through the upper portion of the flask 62. The second tube 70 is interconnected to vacuum source (not shown). De-airing of the chamber of the dilatometer device 10 occurs when the vacuum source draws air from the flask 62. The reduced partial pressures between the flask 62 and the dilatometer 10 causes entrapped air within the aggregate 52 of the dilatometer 10 to be released and drawn into the flask 62 through the first tube 68. Such captured air will bubble up through the water 64 and be drawn by the vacuum source through the second tube 70.

Following de-airing, the water 50 and aggregate 52 are then brought to a first temperature and allowed to equilibrate. This is typically done by placing the container 12 in a water bath (not shown) that is maintained at the desired temperature. The thermocouple 46 is monitored to ensure that the temperature of water 50 and aggregate 52 is accurately maintained. The thermocouple 46 is used as it is preferred to obtain a direct reading of the temperature within the container 12 than to assume that the temperature within the container 12 is the same as that of the water bath outside the container 12.

Once the water 50 and aggregate 52 have equilibrated, the float 38 will be buoyant upon the water level 56 which will be at a first position within the tower member 24. As a result, the LVDT 36 will provide a first reading indicative of the position of the water level 56 within the tower member 24.

The container 12 is brought to a second temperature. Again, this is preferably done by the use of a water bath (not shown) that is being maintained at a second temperature. The water 50 and aggregate 52 are allowed to equilibrate at this second temperature. Again, the thermocouple 46 is used to monitor the temperature of the water 50 and aggregate 52. Once the water 50 and aggregate 52 have equilibrated at this second temperature, the water level 56 and float 38 are brought to a second position within the tower member 24. The LVDT 36 provides a second reading indicative of this second position. The second temperature is higher than the first temperature, and both the water 50 and the aggregate 52 expand as they are brought from the first temperature to the second temperature. An expansion curve is developed to provide the coefficient of thermal expansion for the dilatometer 10 and water 50. That coefficient is then compared to an expansion curve developed during calibration where the container 12 is filled only with water. The coefficient of thermal expansion for in each instance can then be calculated using volumetric equations that relate the rise of the water level 56 within the tower member 24 to the volumetric increases of water 50 and aggregate 52 due to the changes in temperature. For example, when the temperature is raised from $T_1$ to $T_2$, the aggregate 52, the water 50, and the container 12 all expand. Therefore, the apparent volume change that the LVDT 36 detects consists of three parts:

$$\Delta V_1 = A\Delta h = \Delta V_a + \Delta V_w - \Delta V_f$$

where $\Delta V_1$=observed total volumetric increase due to temperature change $\Delta T$, A=inner sectional area of tower, $\Delta h$=rise of the water surface inside the tower, $\Delta V_w$=volumetric increase of water due to change in temperature $\Delta T$, $\Delta V_f$=volumetric increase of inside volume of the dilatometer due to $\Delta T$, $\Delta V_a$=volumetric increase of aggregate $V_a$ due to $\Delta T$, and $\Delta T$=temperature increase from $T_1$ to $T_2$.

Since $$V_f = V_a + V_w = V,$$

$$\Delta V_a = V_a \gamma_a \Delta T$$

$$\Delta V_f = V \gamma_f \Delta T \text{ and}$$

$$\Delta V_w = V_w \gamma_w \Delta T = (V - V_a) \gamma_w \Delta T$$

where V=total inner volume of the container 12,
  $V_w$=volume of water in the container 12,
  $V_f$=volume of the container 12,
  $V_a$=volume of aggregate in the container 12,
  $\gamma_a$=coefficient of volumetric thermal expansion of aggregate,
  $\gamma_w$=coefficient of volumetric thermal expansion of water, and
  $\gamma_f$=coefficient of volumetric thermal expansion of container,
we have $$V_a \gamma_a \Delta T + (V - V_a) \gamma_w \Delta T = \Delta V_1 + V \gamma_f T$$

or $$\gamma_a = \frac{\Delta V_1}{V_a \Delta T} - \left(\frac{V}{V_a} - 1\right)(\gamma_w - \gamma_f) + \gamma_f$$

It can be seen from the latter equation that, in addition to the records of $\Delta V_1$, $T_1$ and $T_2$, one needs to know the coefficients $\gamma_w$ and $\gamma_f$ due to the temperature increase from $T_1$ to $T_2$ in order to determine the coefficient of thermal expansion of the aggregate 52. Those of skill in the art will recognize that the parameter $\gamma_w$ for any temperature range within 0–60° C. can be obtained as:

$$\gamma_w = \frac{v_2 - v_1}{T_2 - T_1}$$

where $v_1$ and $v_2$ are the specific volumes of water at temperatures $T_1$ and $T_2$, respectively.

Figure 3:
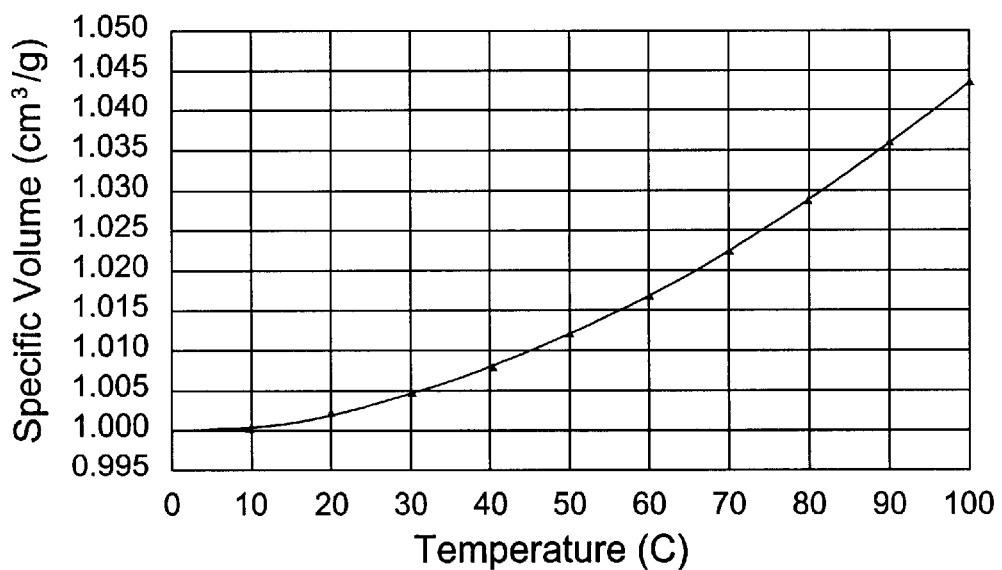
FIG. 3 is a regression table illustrating the volumetric thermal expansion of water.

A regression from these data, illustrated in FIG. 3, shows how the specific volume (the reciprocal of the density) changes with temperature. The coefficient of expansion for the container 12 may be determined by performing a calibration of the dilatometer device 10. Calibration is performed by filling the chamber 14 of the container 12 with distilled water and heating the container 12 in a water bath over a continuous temperature range from 4° C. to 34° C. A temperature increment of about 6° C. has been used in testing. After each temperature increment in the water bath, a minimum of one hour was allowed for the container 12, and the water in it to reach equilibrium in temperature. The temperature, as measured by the thermocouple 46 and the amount of expansion of the distilled water, as measured by the LVDT apparatus 36, were recorded by a computer data acquisition system which was also used to perform the calculations for determining the coefficient of expansion $\gamma_w$.

Figure 4:
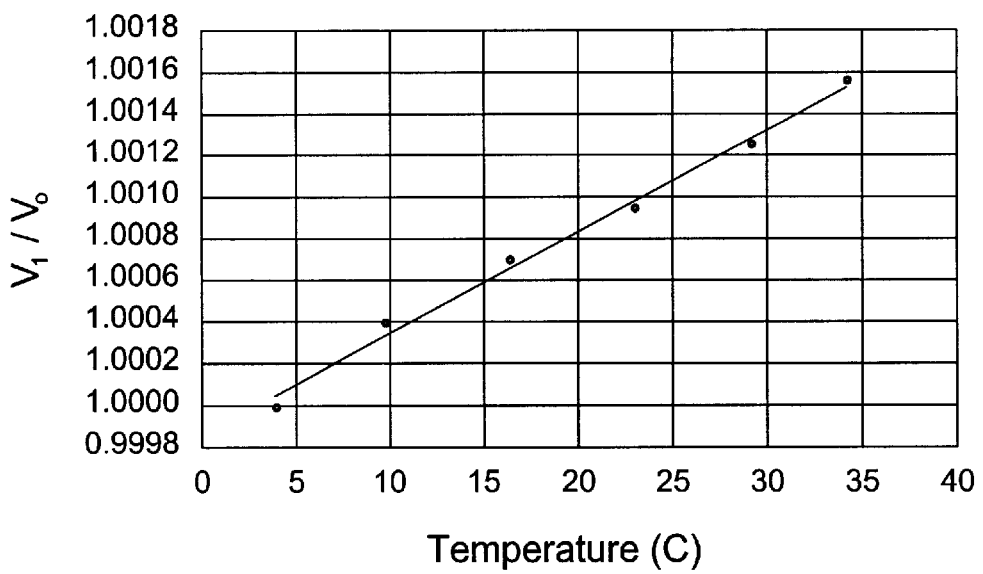
FIG. 4 is a table illustrating the volumetric change of a dilatometer container with temperature.

The coefficient of expansion $\gamma_f$ for the container 12 may be taken as a constant equal to the slope of the straight line $4.90 \times 10^{-5}/°$ C., as depicted in FIG. 4. This value has been obtained empirically, and it is suggested that, if required to achieve the desired degree of precision, empirical testing of the actual container to be used be conducted to obtain more accurate data.

The dilatometer device 10, or a variant thereof, may also be used for methods of testing aggregate expansion that involves chemical treatment of the aggregates instead of variations in temperature. When chemical treatment is used, the float 38 should not be made of glass, but rather, of a material, such as a plastic, that will not react with the particular chemicals that are being applied to the aggregate 52.

For a chemical reactivity test; the water 50 is replaced by an alkali/water solution 50. A currently preferred solution is a one molar sodium oxide solution. Pores within the aggregate 52 contain silica (not shown). Alkali within the solution 50' reacts with the silica and is absorbed into it causing the aggregate 52 to swell. The swelling of the aggregate 52 results in a movement of the water/solution level 56 within the tower member 24.

The dilatometer 10 and associated components will measure the expansion associated with these reactions by detecting the amount of expansion of the mixture of the solution 50' and aggregate 52 caused by reaction of the alkali solution with the silica in the aggregate 52. The degree or percent of volumetric expansion for the aggregate 52 maybe derived using equations similar to those useful for determining coefficients relating to thermal expansion.

The devices and methods of the present invention provide a number of advantages. First, they permit continuous monitoring of both temperature and expansion information for a given aggregate in testing for susceptibility to ASR. The method also allows for a variety of treatments to be applied to the solution 50' relative to their effectiveness to mitigate expansion to ASR. Also, they provide resilient and reusable testing equipment that is capable of testing large, uncrushed portions of aggregates or concrete portions.

While described in terms of a preferred embodiment, those of skill in the art will understand that many modifications and changes may be made while remaining within the scope of the invention.

What is claimed is:

1. A dilatometer for determining information relating to the amount of expansion of an aggregate material, comprising:
   a container housing defining an interior chamber of the housing;
   a lid for enclosing the interior chamber of the housing;
   a buoyant float retained within the lid to contact contents of the interior chamber;
   a transducer operably interconnected with the buoyant float for determining an amount of expansion for material contained within the container housing; and
   a thermocouple for monitoring the temperature within the container housing.

2. The dilatometer of claim 1 wherein the transducer comprises a linear variable differential transducer.

3. The dilatometer of claim 1 wherein the thermocouple comprises a sensing element that extends into the interior chamber of the container.

4. The dilatometer of claim 1 further comprising a data storage device operably interconnected to the apparatus for determining the amount of expansion for recording data indicative of an amount of expansion.

5. The dilatometer of claim 1 wherein the lid retains a tower structure that houses the transducer.

6. A dilatometer for determining information relating to the amount of expansion of an aggregate material, comprising:
   a cylindrical metallic container defining an interior chamber and having an enlarged opening with a diameter of at least six inches to permit insertion of larger samples of aggregate into the chamber;

a lid that is removably affixable to the container to enclose the interior chamber;

a buoyant float retained within the lid to contact contents of the interior chamber; and a transducer operably interconnected with the buoyant float for detecting an amount of change in volume in contents of the interior chamber.

7. The dilatometer of claim 6 further comprising a thermocouple retained within the lid for detecting temperature within the chamber of the container.

8. The dilatometer of claim 6 wherein the transducer and float are retained within a tower structure that extends above the lid.

9. The dilatometer of claim 6 further comprising a device operably interconnected with the transducer and thermocouple for recording data relating to temperature and volume change.

10. A method for determining the coefficient of expansion for a aggregate comprising the steps of:

placing an aggregate with liquid inside of a dilatometer container;

causing the aggregate and liquid to change in volume within the container;

measuring the amount of change in volume for the aggregate and liquid;

determining the amount of change in volume of the aggregate; and deriving a coefficient of expansion for the aggregate.

11. The method of claim 10 wherein the liquid comprises water and the step of causing the aggregate and liquid to change in volume comprises changing the temperature of the aggregate and liquid.

12. The method of claim 11 further comprising the step of monitoring a change in temperature for aggregate and liquid within the chamber.

13. The method of claim 10 wherein the liquid comprises a solution containing sodium oxide and the step of causing the aggregate and liquid to change in volume comprises absorbing alkali from the solution into the aggregate.

14. The method of claim 10 further comprising the step of calibrating the dilatometer container prior to causing the volume change.

15. The method of claim 10 further comprising the step of de-airing the aggregate and liquid prior to causing the change in volume.

* * * * *